United States Patent [19]
Hughes et al.

[11] Patent Number: 6,008,171
[45] Date of Patent: Dec. 28, 1999

[54] CLEANSING COMPOSITIONS

[75] Inventors: Iain Allan Hughes, Surrey; Elizabeth Mary Ryan, Isleworth; Christopher David White, Surrey, all of United Kingdom

[73] Assignee: The Procter & Gamble Company, Cincinnati, Ohio

[21] Appl. No.: 08/860,059

[22] PCT Filed: Nov. 21, 1995

[86] PCT No.: PCT/US95/15142

§ 371 Date: Aug. 21, 1997

§ 102(e) Date: Aug. 21, 1997

[87] PCT Pub. No.: WO96/19554

PCT Pub. Date: Jun. 27, 1996

[30]     Foreign Application Priority Data

Dec. 22, 1994 [GB] United Kingdom ................... 9425932

[51] Int. Cl.⁶ ............................. C11D 3/39; C11D 3/395
[52] U.S. Cl. ..................... 510/117; 510/375; 510/378; 510/466; 424/44; 424/53; 424/54
[58] Field of Search ................................ 510/117, 375, 510/378, 466; 424/44, 53, 54

[56]         References Cited

U.S. PATENT DOCUMENTS

| | | | |
|---|---|---|---|
| 3,607,759 | 9/1971 | Barth | 252/100 |
| 4,155,868 | 5/1979 | Kaplan et al. | 252/95 |
| 4,994,593 | 2/1991 | Lin et al. | 556/424 |
| 5,078,988 | 1/1992 | Lin et al. | 424/49 |
| 5,154,915 | 10/1992 | Weber et al. | 424/54 |
| 5,188,822 | 2/1993 | Viccaro et al. | 424/52 |
| 5,427,770 | 6/1995 | Viccaro et al. | 424/54 |

*Primary Examiner*—Paul Lieberman
*Assistant Examiner*—Gregory R. Del Cotto
*Attorney, Agent, or Firm*—Betty J. Zea; Mary Cay Hentz; Douglas C. Mohl

[57]         ABSTRACT

A denture cleansing composition comprising an inorganic persalt bleaching agent, an effervescence generator and an aminoalkysilicone. The composition provides improved antiplaque, cleasing and antibacterial activity together with excellent physical and in-use performance characteristics.

13 Claims, No Drawings

CLEANSING COMPOSITIONS

TECHNICAL FIELD

The present invention relates to cleansing compositions and especially to compositions for use in cleansing dentures and the like. In particular, the invention relates to denture cleansing compositions having enhanced antiplaque activity together with excellent denture cleansing performance, appearance, physical and dissolution characteristics, antibacterial efficacy and in-use performance characteristics.

BACKGROUND

Effervescent tablets and powders for cleansing dentures and the like are well known in the art. The aim of a denture cleanser product is to clean the denture as fully and as quickly as possible and especially to remove the accumulation of plaque, mucilaginous and bacterial deposits which collect while the denture is being worn. To wear a denture which has not been completely cleaned of plaque and bacterial deposits is not only unhygenic but can also within a short space of time result in a detrimental effect on the mucous membrane. Moreover bacterial deposits can lead to so-called bacterial corrosion of the plastics material used to produce the denture with consequent color-change and malodor-formation.

It is known to include silicones in dentifrice compositions, allegedly to coat the teeth and prevent cavities and staining. For instance, GB-A-689,679 discloses a mouthwash containing an organopolysiloxane for preventing adhesion of, or for removing tars, stains, tartar and food particles from the teeth.

U.S. Pat. No. 2,806,814 discloses dental preparations including, in combination, a higher aliphatic acyl amide of an amino carboxylic acid compound as an active and a silicone compound. The patent notes that silicone compounds have been proposed for prevention of adhesion or to facilitate the removal of tars, stains, tartar and the like from teeth. The silicone compound is said to act as a synergist in improving the antibacterial and acid inhibiting activity of the active ingredient. Dimethyl polysiloxanes are said to be particularly effective.

U.S. Pat. No. 3,624,120 discloses quaternary ammonium salts of cyclic siloxane polymers for use as cationic surfactants, bactericides and as anticariogenic agents.

Dentures of course are generally made of a plastics material such as acrylic and the problem of preventing plaque accumulation or of removing plaque from dentures is therefore fundamentally different from the problem of plaque prevention and removal from dental enamel.

Accordingly, the present invention provides a denture cleanser having improved efficacy on plaque, mucilaginous and bacterial deposits and which at the same time provides excellent denture cleansing performance, appearance, physical characteristics, dissolution and in-use performance characteristics.

SUMMARY OF THE INVENTION

According to a first aspect of the invention, there is provided a denture cleansing composition comprising an inorganic persalt bleaching agent, an effervescence generator and an aminoalkylsilicone as antiplaque agent. The present invention also relates to the use of the defined aminoalkylsilicone as antiplaque agent in denture cleansing compositions All percentages and ratios herein are by weight of total composition, unless otherwise indicated.

The cleansing compositions of the invention thus comprise three essential components, a bleaching agent, an aminoalkylsilicone and an effervescent base composition. Each of these will be discussed in turn.

The bleaching agent takes the form of an inorganic persalt and can be selected from any of the well-known bleaching agents known for use in denture cleansers such as the alkali metal and ammonium persulfates, perborates, percarbonates and perphosphates and the alkali metal and alkaline earth metal peroxides. Examples of suitable bleaching agents include potassium, ammonium, sodium and lithium persulfates and perborate mono- and tetrahydrates, sodium pyrophosphate peroxyhydrate and magnesium, calcium, strontium and zinc peroxides. Of these, however, the alkali metal persulfates, perborates and mixtures thereof are prefered for use herein, highly preferred being the alkali metal perborates. Indeed, it is a feature of the invention that the tablet compositions herein will provide excellent antimicrobial activity even in the absence of alkali metal persulfates.

The amount of bleaching agent in the total composition is generally from about 5 to about 70% preferably from about 10% to about 50%. In compositions comprising a mixture of alkali metal persulfates and perborates, the overall persulfate:perborate ratio is suitably from about 5:1 to about 1:5, more especially from about 2:1 to about 1:2.

The compositions herein also contain an aminoalkylsilicone antiplaque agent. In general terms, the aminoalkylsilicone is selected from noncyclic, hydrophobic aminoalkysilicones having a formula comprising two basic units:

1) $(R^1)_m(R)_n SiO_{(4-m-n)/2}$ wherein m+n is 1, 2 or 3; n is 1, 2 or 3; m is 0,1,2; and 2) $(R^1)_a(R^2)_b SiO_{(4-a-b)/2}$ wherein a+b is 1, 2, or 3, and a and b are integers, wherein $R^1$ and $R^2$ are independently selected from H, alkyl and alkenyl of about 1 to about 10 carbons optionally substituted with fluoro or cyano groups, hydroxy, alkoxy, and acetoxy, for example, wherein $R^1$ and $R^2$ are independently selected from methyl, ethyl, phenyl, vinyl, trifluoropropyl and cyanopropyl, and R is

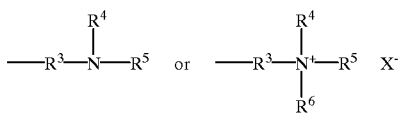

wherein $R^3$ is a divalent alkylene of about 1–20, preferably about 3–5 carbon atoms optionally substituted or interrupted by O atoms, $R^4$, $R^5$ and $R^6$ which may be the same or different are selected from H, alkyl of about 1–20, preferably about 1–10, more preferably about 1–4 carbons optionally substituted or interrupted by N and/or O atoms, and X is a monovalent anion such as halide, hydroxide, and tosylate, said aminoalkylsilicone including about 60% or less, preferably from about 0.1–30%, more preferably from 0.2–10% and especially from about 0.5–2% of unit (1) on a repeating unit basis.

In a preferred embodiment, the aminoalkylsilicones comprise amodimethicones. Amodimethicones are polydimethylsiloxane polymers containing aminoalkyl groups. The aminoalkyl groups may be present either pendant or at one or more ends of the polydimethylsiloxane chain. Preferred are aminoalkylsilicones in which aminoalkyl moiety R is selected from $(CH_2)_3NH_2$, $(CH_2)_3NHCH_2CH_2NH_2$, $(CH_2)_3N(CH_2CH_2OH)_2$, $(CH_2)_3NH_3^+X^-$, and $(CH_2)_3N(CH_3)_2(C_{18}H_{37})^+X^-$, and especially from $(CH_2)_3NH_2$ and $(CH_2)_3NHCH_2CH_2NH_2$. Also preferred are aminoalkyl silicones having an average molecular weight of about 5,000 and above, preferably from about 5000 to about 100,000, more preferably from about 5000 to about 30,000.

Aminoalkylsilicone compounds suitable for use herein are well known. Methods of preparing aminoalkylsilicones are given in, for example, U.S. Pat. No. 2,930,809.

Examples of amodimethicones include Dow Corning's DC-929, DC-Q2-7224 and Q2-8075 and OSI's Magnasoft fluid, the latter being preferred. These polymers comprise aminoalkyl groups affixed to a predominantly polydimethylsiloxane structure. The typical structure of Magnasoft's aminoalkyl group-containing units is

—OSi(Me)C$_3$H$_6$NHCH$_2$CH$_2$NH$_2$.

The aminoalkylsilicone is generally present in a level of from about 0.01% to about 25%, preferably from about 0.1% to about 5%, more preferably from about 0.5% to about 1.5% by weight.

The denture cleansing compositions also incorporate an effervescence generator which in preferred embodiments takes the form of a solid base material which in the presence of water releases carbon dioxide or oxygen with effervescence. The effervescence generator utilized in the compositions herein can be selected from generators which are effective under acid, neutral or alkaline pH conditions, but preferably it consists of a combination of a generator which is effective or most effective under acid or neutral pH conditions and a generator which is effective or most effective under alkaline pH conditions. Effervescence generators which are effective under acid or neutral pH conditions include a combination of at least one alkali metal carbonate or bicarbonate, such as sodium bicarbonate, sodium carbonate, sodium sesquicarbonate, potassium carbonate, potassium bicarbonate, or mixtures thereof, in admixture with at least one non-toxic, physiologically-acceptable organic acid, such as tartaric, fumaric, citric, malic, maleic, gluconic, succinic, salicylic, adipic or sulphamic acid, sodium fumarate, sodium or potassium acid phosphates, betaine hydrochloride or mixtures thereof. Of these, malic acid is preferred. Effervescence generators which are effective under alkaline pH conditions include persalts such as alkali and alkaline earth metal peroxoborates as well as perborates, persulphates, percarbonates, perphosphates and mixtures thereof as previously described, for example, a mixture of an alkali metal perborate (anhydrous, mono- or tetrahydrate) with a monopersulphate such as Caroat $^R$ marketed by E I du Point de Nemours Co. and which is a 2:1:1 mixture of monopersulphate, potassium sulphate and potassium bisulphate and which has an active oxygen content of about 4.5%.

In highly preferred compositions, the solid base material incorporates a (bi)carbonate/acid effervescent couple optionally in combination with a perborate/persulphate oxygen effervescence generator. The combination of generators is valuable for achieving optimum dissolution characteristics and pH conditions for achieving optimum cleaning and antimicrobial activity. The (bi)carbonate components generally comprise from about 5% to about 65%, preferably from about 25% to 55% of the total composition; the acid components generally comprise from about 5% to about 50%, preferably from about 10% to about 30% of the total composition.

The compositions of the invention can be supplemented by other known components of denture cleansing formulations. An especially preferred additional component is an organic peroxyacid precursor, which in general terms can be defined as a compound having a titre of at least 1.5 ml of 0.1 N sodium thiosulfate in the following peracid formation test.

A test solution is prepared by dissolving the following materials in 1000 mls distilled water:

| | |
|---|---|
| sodium pyrophosphate (Na$_4$P$_2$O$_7$.10H$_2$O) | 2.5 g |
| sodium perborate (NaBO$_2$.H$_2$O$_2$.3H$_2$O) having 10.4% available oxygen | 0.615 g |
| sodium dodecylbenzene sulphonate | 0.5 g |

To this solution at 60° C. an amount of activator is added such that for each atom of available oxygen present one molecular equivalent of activator is introduced.

The mixture obtained by addition of the activator is vigorously stirred and maintained at 60° C. After 5 minutes from addition, a 100 ml portion of the solution is withdrawn and immediately pipetted onto a mixture of 250 g cracked ice and 15 ml glacial acetic acid. Potassium iodide (0.4 g) is then added and the liberated iodine is immediately titrated with 0.1 N sodium thiosulphate with starch as indicator until the first disappearance of the blue colour. The amount of sodium thiosulphate solution used in ml is the titre of the bleach activator.

The organic peracid precursors are typically compounds containing one or more acyl groups, which are susceptible to perhydrolysis. The preferred activators are those of the N-acyl or O-acyl compound type containing a acyl radical R—CO wherein R is a hydrocarbon or substituted hydrocarbon group having preferably from about 1 to about 20 carbon atoms. Examples of suitable peracid precursors include:

1) Acyl organoamides of the formula RCONR$_1$R$_2$, where RCO is carboxylic acyl radical, R$_1$ is an acyl radical and R$_2$ is an organic radical, as disclosed in U.S. Pat. No. 3,117,148. Examples of compounds falling under this group include:
   a) N,N-diacetylaniline and N-acetylphthalimide;
   b) N-acylhydantoins, such as N,N'-diacetyl-5,5-dimethylhydantoin;
   c) Polyacylated alkylene diamines, such as N,N,N'N'-tetraacetylethylenediamine (TAED) and the corresponding hexamethylenediamine (TAHD) derivatives, as disclosed in GB-A-907,356, GB-A-907,357 and GB-A-907,358;
   d) Acylated glycolurils, such as tetraacetylglycoluril, as disclosed in GB-A-1,246,338, GB-A-1,246,339 and GB-A-1,247,429.

2) Acylated sulphonamides, such as N-methyl-N-benzoyl-menthane sulphonamide and N-phenyl-N-acetyl menthane sulphonamide, as disclosed in GB-A-3,183,266.

3) Carboxylic esters as disclosed in GB-A-836,988, GB-A-963,135 and GB-A-1,147,871. Examples of compounds of this type include phenyl acetate, sodium acetoxy benzene sulphonate, trichloroethylacetate, sorbitol hexaacetate, fructose pentaacetate, p-nitrobenzaldehyde diacetate, isopropeneyl acetate, acetyl aceto hydroxamic acid, and acetyl salicylic acid. Other examples are esters of a phenol or substituted phenol with an alpha-chlorinated lower aliphatic carboxylic acid, such as chloroacetylphenol and chloroacetylsalicylic acid, as disclosed in U.S. Pat. No. 3,130, 165.

4) Carboxylic esters having the gernal formal Ac L wherein Ac is the acyl moiety of an organic carboxylic acid comprising an optionally substituted, linear or branched $C_6$–$C_{20}$ alkyl or alkenyl moiety or a $C_6$–$C_{20}$ alkyl-substituted aryl moiety and L is a leaving group, the conjugate acid of which has a pKa in the range from 4 to 13, for example oxybenzenesulfonate or oxybenzoate. Preferred compounds of this type are those wherein:

a) Ac is $R_3$—CO and $R_3$ is a linear or branched alkyl group containing from 6 to 20, preferably 6 to 12, more preferably 7 to 9 carbon atoms and wherein the longest linear alkyl chain extending from and including the carbonyl carbon contains from 5 to 18, preferably 5 to 10 carbon atoms, $R_3$ optionally being substituted (preferably alpha to the carbonyl moiety) by Cl, Br, OCH3 or $OC_2H_5$. Examples of this class of material include sodium 3,5,5-trimethylhexanoyloxybenzene sulfonate, sodium 3,5,5-trimethylhexanoyloxybenzoate, sodium 2-ethylhexanoyl oxybenzenesulfonate, sodium nonanoyl oxybenzene sulfonate and sodium octanoyl oxybenezenesulfonate, the acyloxy group in each instance preferably being p-substituted;

b) Ac has the formula $R_3(AO)_m XA$ wherein $R_3$ is a linear or branched alkyl or alkylaryl group containing from 6 to 20, preferably from 6 to 15 carbon atoms in the alkyl moiety, $R_5$ being optionally substituted by Cl, Br, $OCH_3$, or $OC_2H_5$, AO is oxyethylene or oxypropylene, m is from 0 to 100, X is O, $NR_4$ or CO—$NR_4$, and A is CO, CO—CO, $R_6$—CO, CO—$R_6$—CO, or CO—$NR_4$—$R_6$—CO wherein $R_4$ is $C_1$-$C_4$ alkyl and $R_6$ is alkylene, alkenylene, arylene or alkarylene containing from 1 to 8 carbon atoms in the alkylene or alkenylene moiety. Bleach activator compounds of this type include carbonic acid derivatives of the formula $R_3(AO)_m OCOL$, succinic acid derivatives of the formula $R_3OCO(CH_2)_2COL$, glycollic acid derivatives of the formula $R_3OCH_2COL$, hydroxypropionic acid derivatives of the formula $R_3OCH_2CH_2COL$, oxalic acid derivatives of the formula $R_3OCOCOL$, maleic and fumaric acid derivatives of the formula $R_3OCOCH=CHCOL$, acyl aminocaproic acid derivatives of the formula $R_3CONR_1(CH_2)_6COL$, acyl glycine derivatives of the formula $R_3CONR_1CH_2COL$, and amino-6-oxocaproic acid derivatives of the formula $R_3N(R_1)CO(CH_2)_4COL$. In the above, m is preferably from 0 to 10, and $R_3$ is preferably $C_6$–$C_{12}$, more preferably $C_6$–$C_{10}$ alkyl when m is zero and $C_9$–$C_{15}$ when m is non-zero. The leaving group L is as defined above.

5) Acyl-cyanurates, such as triacetyl- or tribenzoylcyanurates, as disclosed in US patent specification No. 3,332,882.

6) Optionally substituted anhydrides of benzoic or phthalic acid, for example, benzoic anhydride, m-chlorobenzoic anhydride and phthalic anhydride.

Of all the above, preferred are organic peracid precursors of types 1(c) and 4(a).

Where present, the level of peroxyacid bleach precursor by weight of the total composition is preferably from about 0.1% to about 10%, more preferably from about 0.5% to about 5% and is generally added in the form of a bleach precursor agglomerate.

The bleach precursor agglomerates preferred for use herein generally comprise a binder or agglomerating agent in a level of from about 5% to about 40%, more especially from about 10% to about 30% by weight thereof. Suitable agglomerating agents include polyvinylpyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, phosphates and polyphosphates, clays, aluminosilicates and polymeric polycarboxylates. Of the above, polyethyleneglycols are highly preferred, especially those having molecular weight of from about 1,000 to about 30,000, preferably 2000 to about 10,000.

Preferred from the viewpoint of optimum dissolution and pH characteristics are bleach precursor agglomerates which comprise from about 10% to about 75%, preferably from about 20% to about 60% by weight thereof of peroxyacid bleach precursor, from about 5% to about 60% preferably from about 5% to about 50%, more preferably from about 10% to about 40% of a (bi) carbonate/acid effervescent couple, from about 0% to about 20% of a peroxoboroate, and from about 5% to about 40%, preferably from about 10% to about 30% of an agglomerating agent.

The final bleach precursor granules desirably have an average particle size of from about 500 to about 1500, preferably from about 500 to about 1,000 µm, this being valuable from the viewpoint of optimum dissolution performance and aesthetics. The level of bleach precursor agglomerates, moreover, is preferably from about 1% to about 20%, more preferably from about 5% to about 15% by weight of composition.

The compositions of the invention can be in paste, liquid, tablet, granular or powder form, although tablet-form compositions are highly preferred herein. Compositions in tablet form can be single or multiple layered tablets.

The compositions of the invention can be supplemented by other usual components of denture cleansing formulations, especially surfactants, chelating agents, enzymes, flavorants, physiological cooling agents, antimicrobial compounds, dyestuffs, sweeteners, tablet binders and fillers, foam depressants such as dimethylpolysiloxanes, foam stabilizers such as the fatty acid sugar esters, preservatives, lubricants such as talc, magnesium stearate, finely divided amorphous pyrogenic silicas, etc. The free moisture content of the final composition is desirably less than about 1% and especially less than about 0.5%.

Tablet binders and fillers suitable for use herein include polyvinylpyrrolidone, poly (oxyethylene) of molecular weight 20,000 to 500,000, polyethyleneglycols of molecular weight of from about 1000 to about 50,000, Carbowax having a molecular weight of from 4000 to 20,000, nonionic surfactants, fatty acids, sodium carboxymethyl cellulose, gelatin, fatty alcohols, clays, polymeric polycarboxylates, sodium carbonate, calcium carbonate, calcium hydroxide, magnesium oxide, magnesium hydroxide carbonate, sodium sulfate, proteins, cellulose ethers, cellulose esters, polyvinyl alcohol, alginic acid esters, vegetable fatty materials of a pseudocolloidal character. Of the above, polyethyleneglycols are highly preferred, especially those having molecular weight of from about 1,000 to about 30,000, preferably from about 12,000 to about 30,000.

The surface active agent used in the compositions of the invention can be selected from the many available that are compatible with the other ingredients of the denture cleanser, both in the dry state and in solution. Such materials are believed to improve the effectiveness of the other ingredients of the composition by aiding their penetration into the interdental surfaces. Also, these materials aid in the removal of food debris attached to the teeth. Between 0.1 and 5 percent by weight of the dry composition of a dry powder or granular anionic surface active agent, such as sodium lauryl sulfate, sodium N-lauroylsarcosinate, sodium lauryl sulfoacetate or dioctyl sodium sulfosuccinate or ricinoleyl sodium sulfosuccinate, may, for example, be included in the composition and preferably the surface active agent comprises between 0.5 and 4 percent of the composition.

Suitable cationic, non-ionic and ampholytic surface active agents include, for example, quaternary ammonium compounds such as cetyltrimethylammonium bromide, condensation products of alkylene oxides such as ethylene or propylene oxide with fatty alcohols, phenols, fatty amines or fatty acid alkanolamides, the fatty acid alkanolamides themselves, esters of long-chained ($C_8$–$C_{22}$) fatty acids with polyalcohols or sugars, for example glycerylmonostearate or saccharosemonolaurate or sorbitolpolyoxyethylenemono-or di-stearate, betaines, sulphobetaines or long-chain alkylaminocarboxylic acids.

Chelating agents beneficially aid cleaning and bleach stability by keeping metal ions, such as calcium, magnesium, and heavy metal cations in solution. Examples of suitable chelating agents include sodium tripolyphosphate, sodium acid pyrophosphate, tetrasodium pyrophosphate, aminopolycarboxylates such as nitrilotriacetic acid and ethylenediamine tetracetic acid and salts thereof, and polyphosphonates and aminopolyphosphonates such as hydroxyethanediphosphonic acid, ethylenediamine tetramethylenephosphonic acid, diethylenetriaminepentamethylenephosphonic acid and salts thereof. The chelating agent selected is not critical except that it must be compatible with the other ingredients of the denture cleanser when in the dry state and in aqueous solution. Advantageously, the chelating agent comprises between 0.1 and 60 percent by weight of the composition and preferably between 0.5 and 30 percent. Phosphonic acid chelating agents, however, preferably comprise from about 0.1 to about 1 percent, preferably from about 0.1% to about 0.5% by weight of composition.

Enzymes suitable for use herein are exemplified by proteases, alkalases, amylases, lipases, dextranases, mutanases, glucanases etc.

Flavorants suitable for use in the compositions of the invention include wintergreen oil, oregano oil, bay leaf oil, peppermint oil, spearmint oil, clove oil, sage oil, sassafras oil, lemon oil, orange oil, anise oil, benzaldehyde, bitter almond oil, camphor, cedar leaf oil, marjoram oil, citronella oil, lavendar oil, mustard oil, pine oil, pine needle oil, rosemary oil, thyme oil, cinnamon leaf oil, and mixtures thereof. Suitable antimicrobial compounds include thymol, menthol, triclosan, 4-hexylresorcinol, phenol, eucalyptol, benzoic acid, benzoyl peroxide, butyl paraben, methyl paraben, propyl paraben, salicylamides, and mixtures thereof.

The following Examples further describe and demonstrate the preferred embodiments within the scope of the present invention.

EXAMPLES I TO V

The following are representative denture cleansing tablets according to the invention. The percentages are by weight of the total tablet. The tablets are made by compressing a mixture of the granulated components in a punch and dye tabletting press at a pressure of about $10^5$ kPa.

|  | I | II | III | IV | V |
|---|---|---|---|---|---|
| Malic Acid | 12 | 10 | 15 | — | 14 |
| Citric Acid | — | 10 | — | 15 | — |
| Sodium Carbonate | 10 | 8 | 10 | 6 | 10 |
| Sulphamic Acid | 5 | — | — | 3 | 3 |
| PEG 20,000 | — | 3 | 7 | 8 | 5 |
| PVP 40,000 | 6 | 3 | — | — | — |
| Sodium Bicarbonate | 22 | 19 | 24.5 | 13 | 23 |
| Sodium Perborate Monohydrate | 15 | 12 | 16 | 30 | 15 |
| Potassium Monopersulphate | 15 | 18 | 13 | — | 14 |
| Pyrogenic Silica | — | 3 | 1 | 1 | — |
| Talc | 2 | — | — | — | — |
| EDTA | — | — | 1 | — | 3 |
| EDTMP[1] | 1 | — | — | 1 | — |
| Flavor[5] | 2 | 1 | 2 | 1 | 2 |
| Magnasoft Fluid[4] | 1 | 5 | 0.5 | 10 | 1 |
| Bleach Precursor Agglomerate | 9 | 8 | 10 | 12 | 10 |
| Bleach Precursor Agglomerate |  |  |  |  |  |
| TAED[2] | 2 | — | 4 | 5 | 2.5 |
| TMHOS[3] | 2 | 3 | — | — | — |
| Sulphamic Acid | 2 | 2 | 2 | 2 | 3.5 |
| Sodium Bicarbonate | 0.5 | 0.2 | 0.2 | 0.5 | 2 |
| PEG 6000 | 2.5 | 2 | 2.4 | 2.5 | 1.5 |
| Dye | — | 0.8 | 1.4 | 2 | 0.5 |

[1]Ethylenediaminetetramethylenephosphonic acid
[2]Tetraacetylethylene diamine
[3]Sodium 3,5,5-trimethylhexanoyloxybenzene sulfonate
[4]Magnasoft Fluid
[5]Peppermint-based flavor In Examples I to V above, the overall tablet weight is 3 g; diameter 25 mm.

The denture cleansing tablets of Examples I to V display improved antiplaque efficacy together with excellent cleansing and anti-bacterial activity, cohesion and other physical and in-use performance characteristics.

We claim:

1. A denture cleansing composition comprising an inorganic persalt bleaching agent, an effervescence generator an organic peroxyacid bleach precursor and an aminoalkyl silicone wherein the aminoalkylsilicone is a noncyclic hydrophobic aminoalkylsilicone having a formula comprising two basic units:

1) $(R^1)_m(R)_n SiO_{(4-m-n)/2}$ wherein m+n is 1, 2 or 3; n is 1,2 or 3; m is 0,1,2;and
   2) $R^1)_a(R^2)_b SiO_{(4-a-b)/2}$ wherein a+b is 1, 2, or 3, and a and b are integers, wherein $R^1$ and $R^2$ are independently selected from H, alkyl and alkenyl of about optionally substituted with fluoro or cyano groups, hydroxy, alkoxy, and acetoxy, and R is

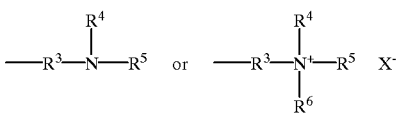

wherein $R^3$ is a divalent alkylene of about 1–20 carbon atoms optionally substituted or interrupted by O atoms, $R^4$, $R^5$ and $R^6$ which may be the same or different are selected from H, alkyl of about 1–20 carbons optionally substituted or interrupted by N and/or O atoms, and $X^-$ is a monovalent anion, said aminoalkyl silicone including about 60% or less of unit (1) on a repeating unit basis.

2. A composition according to claim 1 wherein the aminoalkyl silicone has a molecular weight of at least about 5,000,.

3. A composition according to claim 2 wherein $R^1$ and $R^2$ are independently selected from methyl, ethyl, phenyl, vinyl, trifluoropropyl and cyanopropyl.

4. A composition according to claim 3 wherein $R^3$ is a divalent alkylene having from 3 to 5 carbon atoms.

5. A composition according to claim 4 wherein R is selected from $(CH_2)_3NH_2$, $(CH_2)_3NHCH_2CH_2NH_2$, $(CH_2)_3N(CH_2CH_2OH)_2$, $(CH_2)_3NH_3^+X^-$, and $(CH_2)_3N(CH_3)_2(C_{18}H_{37})^+X^-$.

6. A composition according to claim 5 wherein the aminoalkylsilicone is amodimethicone.

7. A composition according to claim 6 comprising from about 0.01% to about 25%, by weight of the aminoalkylsilicone.

8. A composition according to claim 7 wherein the inorganic persalt bleaching agent comprises one or more bleaching agents selected from alkali metal persulfates, alkali metal perborates and mixtures thereof.

9. A composition according to claim 7 wherein the effervescence generator comprises a (bi)carbonate/acid effervescent couple.

10. A composition according to claim 1 wherein the organic peroxyacid bleach precursor is selected from acylated polyalkyldiamines, especially tetraacetylethylenediamine, and carboxylic esters having the general formula AcL wherein Ac is the acyl moiety or an organic carboxylic acid comprising an optionally substituted, linear or branched $C_6$–$C_{20}$ alkyl or alkenyl moiety or a $C_6$–$C_{20}$ alkyl-substituted aryl moiety and L is a leaving group, the conjugate acid of which has a pKa in the range from 4 to 13.

11. A composition according to claim 2 wherein the aminoalkyl silicone has a molecular weight of at least from about 5000 to about 100,000.

12. A composition according to claim 8 comprising from about 0.1% to about 5% by weight of the aminoalkylsilicone.

13. A method of cleaning dentures by applying to the dentures, a composition comprising an inorganic persalt bleaching agent, an effervescence generator an organic peroxyacid bleach precursor and an aminoalkylsilicone wherein the aminoalkylsilicone is a noncyclic, hydrophobic aminoalkylsilicone having a formula comprising two basic units:

1) $(R^1)_m(R)_nSiO_{(4-m-n)/2}$ wherein m+n is 1, 2 or 3; n is 1, 2 or 3; m is 0,1,2;and 2) $(R^1)_a(R^2)_bSiO_{(4-a-b)/2}$ wherein a+b is 1, 2, or 3, and a and b are integers, wherein $R^1$ and $R^2$ are independently selected from H, and alkenyl of about 1 to about 10 carbons optionally substituted with fluoro or cyano groups, hydroxy, alkoxy, and acetoxy, and R is

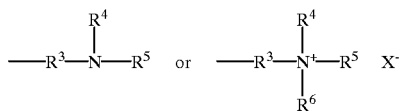

wherein $R^3$ is a divalent alkylene of about 1–20 carbon atoms optionally substituted or interrupted by O atoms, $R^4$, $R^5$ and $R^6$ which may be the same or different are selected from H, alkyl of about 1–20 carbons optionally substituted or interrupted by N and/or O atoms, and X is a monovalent anion, said aminoalkyl silicone including about 60% or less of unit (1)-on a repeating unit basis.

* * * * *